United States Patent
Yamaguchi

(10) Patent No.: US 11,887,827 B2
(45) Date of Patent: Jan. 30, 2024

(54) IMAGING ANALYSIS DEVICE

(71) Applicant: SHIMADZU CORPORATION, Kyoto (JP)

(72) Inventor: Shinichi Yamaguchi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 135 days.

(21) Appl. No.: 17/437,953

(22) PCT Filed: Apr. 24, 2019

(86) PCT No.: PCT/JP2019/017370
§ 371 (c)(1),
(2) Date: Sep. 10, 2021

(87) PCT Pub. No.: WO2020/217335
PCT Pub. Date: Oct. 29, 2020

(65) Prior Publication Data
US 2022/0172936 A1 Jun. 2, 2022

(51) Int. Cl.
H01J 49/00 (2006.01)
(52) U.S. Cl.
CPC .................. H01J 49/0004 (2013.01)
(58) Field of Classification Search
CPC ............ H01J 49/0004; H01J 49/0036; G01N 33/6848
(Continued)

(56) References Cited

U.S. PATENT DOCUMENTS

| 2012/0133671 | A1* | 5/2012 | Setou | G06T 7/0012 345/593 |
| 2016/0071711 | A1* | 3/2016 | Ikegami | H01J 49/0036 250/281 |
| 2019/0272984 | A1 | 9/2019 | Takeshita | |

FOREIGN PATENT DOCUMENTS

| CN | 103620413 A | 3/2014 |
| CN | 107389720 A | 11/2017 |

(Continued)

OTHER PUBLICATIONS

Nhu T. N. Phan et al., "MS/MS analysis and imaging of lipids across *Drosophila* brain using secondary ion mass spectrometry", Analytical and Bioanalytical Chemistry, Jun. 2017, pp. 3923-3932, vol. 409, Issue 16.

(Continued)

Primary Examiner — Michael Maskell
(74) Attorney, Agent, or Firm — Sughrue Mion, PLLC

(57) ABSTRACT

An imaging mass spectrometer according to one aspect of the present invention includes an analysis executing section (1) configured to collect data by executing predetermined analysis on each of a plurality of micro regions set in a two-dimensional measurement region (50) on a sample (50) or a three-dimensional measurement region in the sample; a first image creating section (21) that uses the data obtained by the analysis executing section (1) to create one or a plurality of first distribution images each reflecting a distribution of one or a plurality of specific components included in the sample (50); a formula storage section (23) that stores, as a formula, a chemical reaction formula including at least the one or a plurality of specific components as elements, or a calculation formula including an amount of the specific component as element; a signal value calculating section (25) that calculates different signal values from the signal values in the micro regions constituting the one or the (Continued)

plurality of first distribution images by using the formula acquired from the formula storage section (23) in response to a user's instruction; and a second image creating section (26) that creates a second distribution image based on a calculation result.

8 Claims, 2 Drawing Sheets

(58) Field of Classification Search
USPC .................................................. 250/281, 282
See application file for complete search history.

(56) References Cited

FOREIGN PATENT DOCUMENTS

| | | |
|---|---|---|
| JP | 2009-42835 A | 2/2009 |
| WO | 2012/126873 A1 | 9/2012 |
| WO | 2018/037491 A1 | 3/2018 |

OTHER PUBLICATIONS

"Imagereveal MS", Instruction Manual, Shimadzu Corporation, Jan. 2019, pp. 1-272.
Yuki Mori, "Non-invasive and high-resolution tracking of individual immune cells using the preclinical high-field MRI scanner", Systems, Control and Information, 2017, pp. 340-345, vol. 61, No. 8.
Yoshinori Onuki, "Evaluation of physical stability of emulsion-based formulations using a molecular imaging technique, MRI", The Proceedings of the Hoshi University, 2012, pp. 11-18, vol. 54.
Written Opinion for PCT/JP2019/017370, dated Jul. 9, 2019.
International Search Report for PCT/JP2019/017370, dated Jul. 9, 2019.
Chinese Office Action dated Oct. 28, 2023 in Application No. 201980093558.X.

\* cited by examiner

IMAGING ANALYSIS DEVICE

CROSS REFERENCE TO RELATED APPLICATIONS

This application is a National Stage of International Application No. PCT/JP2019/017370 filed Apr. 24, 2019.

TECHNICAL FIELD

The present invention relates to an imaging analysis device capable of executing analysis by various methods such as mass spectrometry, Raman spectroscopic analysis, infrared spectroscopic analysis, and fluorescence analysis for each of a large number of measurement points (micro regions) within a two-dimensional region on a sample or a three-dimensional region in a sample.

BACKGROUND ART

In the imaging mass spectrometer described in Patent Literature 1 and the like, a two-dimensional intensity distribution of ions having a specific mass-to-charge ratio m/z at the surface of a sample such as a biological tissue section can be measured while observing the form of the surface of the sample with an optical microscope. At this time, an image showing the state of distribution of a specific compound in the sample can be obtained by specifying the mass-to-charge ratio of the ion characteristic of the specific compound to visualize the signal strength distribution.

CITATION LIST

Patent Literature

Patent Literature 1: WO 2018/037491 A

SUMMARY OF INVENTION

Technical Problem

In vivo, various chemical reactions (usually called biochemical reactions) including energy metabolism occur, whereby one compound produces another compound. In the medical field, drug development field, biochemical field, and the like, the distribution of a compound that widely exists at various sites in a living body or locally exist at a specific site by various biochemical reactions need to be examined. The distribution of such a compound can also be acquired by an imaging mass spectrometer.

However, even if a mass-to-charge ratio assumed to correspond to a certain specific compound B is selected and a mass spectrometry image (hereinafter, referred to as an "MS image") showing the intensity distribution of ions of the mass-to-charge ratio value is created, such distribution does not necessarily accurately represent the distribution of the compound B generated by the biochemical reaction with respect to the certain original compound A. This is because in the sample derived from a living body, various compounds exist in addition to the target compound, and ions derived from another compound having the same or similar mass-to-charge ratio as the ions derived from the compound B, which is the basis for creating the MS image, exist, and there is a possibility that regions in which the another compound are distributed overlap. Thus, when the distribution of the compound B is obtained, it is necessary to verify whether or not the distribution is the distribution of the compound B generated by the biochemical reaction with respect to a certain original compound A, but such verification is not easy.

In a living body, energy is produced or energy is consumed accompanying a biochemical reaction such as metabolism. It is important to grasp the distribution of the production amount and the consumption amount of energy in the biological tissue in order to elucidate the mechanism of metabolism and the like. The production amount and the consumption amount of energy can be calculated based on the amount of compounds related to metabolism and the like existing in cells in a biological tissue using a predetermined formula reflecting the biochemical reaction. However, in the conventional imaging mass spectrometer, it is not easy to obtain the distribution of the production amount or consumption amount of energy by metabolism based on the result of imaging mass spectrometry of a sample such as a biological tissue section.

Similar problem applies not only to the imaging mass spectrometer but also to a general imaging analysis device that creates a distribution image using Raman spectroscopic analysis, infrared spectroscopic analysis, fluorescence analysis, or the like.

The present invention has been made to solve such problems, and one object is to provide an imaging analysis device capable of easily evaluating whether or not a distribution of a compound generated by various chemical reactions such as biochemical reactions is accurate. Another object of the present invention is to provide an imaging analysis device capable of easily obtaining a distribution image that has not been easily visualized conventionally, such as a distribution of energy produced or consumed by a chemical reaction such as metabolism.

Solution to Problem

An imaging analysis device according to one aspect of the present invention includes,
an analysis executing section configured to collect data by executing predetermined analysis on each of a plurality of micro regions set in a two-dimensional measurement region on a sample or a three-dimensional measurement region in a sample;
a first image creating section configured to use the data obtained by the analysis executing section to create one or a plurality of first distribution images each reflecting a distribution of one or a plurality of specific components included in the sample;
a formula storage section configured to store a formula which is either a chemical reaction formula including at least the one or a plurality of specific components as elements, or either a calculation formula or a logical formula including an amount of the specific component as an element;
a signal value calculating section configured to calculate a signal value different from the signal value in each of the micro regions constituting the one or the plurality of first distribution images by using the formula acquired from the formula storage section in response to an instruction of a user; and
a second image creating section configured to create a second distribution image based on the calculation result by the signal value calculating section.

In the imaging analysis device according to one aspect of the present invention, as the predetermined analysis, for example, mass spectrometry, Raman spectroscopic analysis, infrared spectroscopic analysis, fluorescence analysis, or the like can be used. In a case where the predetermined analysis is mass spectrometry, the imaging analysis device according to the present invention is an imaging mass spectrometer, and the first distribution image can be a mass spectrometry image showing intensity of ions derived from a specific component (hereinafter, may be referred to as an "MS image") or a density image obtained by converting the ionic intensity into density (content).

Advantageous Effects of Invention

Owing to the imaging analysis device according to one aspect of the present invention, a second distribution image different from a first distribution image can be created based on signal values calculated using the formula stored in advance in the formula storage section, and this can be, for example, displayed on a display unit or printed out. By using a chemical reaction formula as the formula, a distribution image after the chemical reaction reflecting a distribution of, for example, another component which is assumed to be created from one or a plurality of specific components by the chemical reaction can be provided to the user. Alternatively, a distribution of another component before the chemical reaction which is assumed to generate a specific component by the chemical reaction can also be provided to the user. Further, using a calculation formula for obtaining the energy production amount as the formula, for example, an image showing the distribution of the energy production amount can be provided to the user.

DESCRIPTION OF EMBODIMENTS

Hereinafter, an imaging mass spectrometer according to one embodiment of the present invention will be described with reference to the accompanying drawings.

Configuration of Device of Present Embodiment

Figure 1:
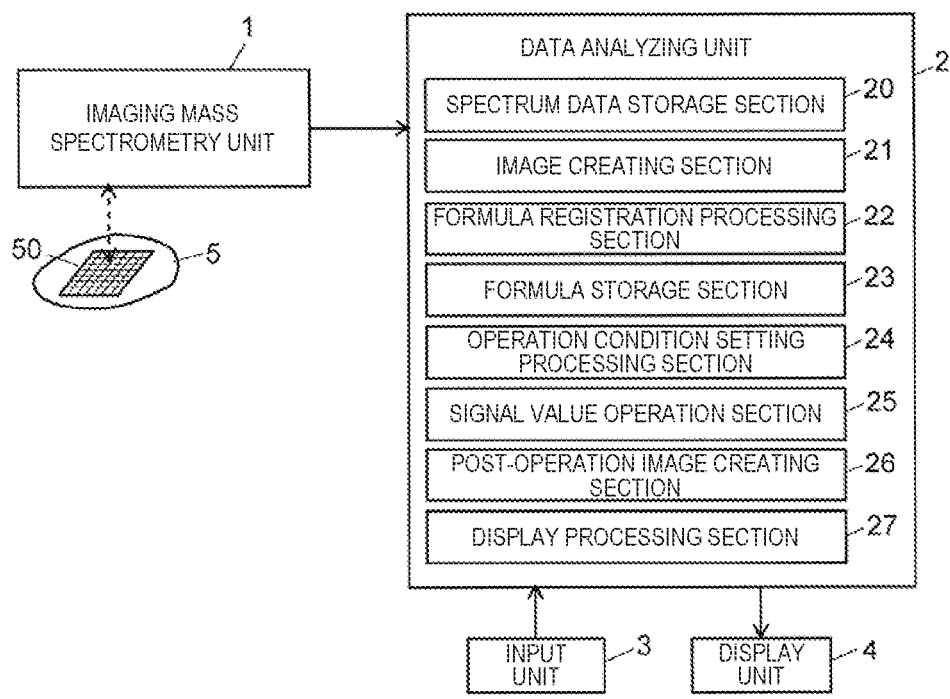
FIG. 1 is a configuration diagram of a main part of an imaging mass spectrometer according to one embodiment of the present invention.

FIG. 1 is a schematic block configuration diagram of an imaging mass spectrometer of the present embodiment.

The imaging mass spectrometer of the present embodiment includes an imaging mass spectrometry unit 1, a data analyzing unit 2, an input unit 3, and a display unit 4.

Although not illustrated, the imaging mass spectrometry unit 1 includes, for example, an ion source by an atmospheric pressure matrix-assisted laser desorption ionization (AP-MALDI) method for irradiating a sample with laser light under an atmospheric pressure atmosphere to ionize a substance in the sample, an ion trap for temporarily trapping ions derived from a sample component, a mass separation unit for separating ions discharged from the ion trap with high mass accuracy and mass resolution, and a detection unit for detecting the separated ions. As the mass separation unit, for example, a time-of-flight mass spectrometer or a Fourier transform mass spectrometer such as a Fourier transform ion cyclotron resonance (FT-ICR) type can be used.

In the imaging mass spectrometry unit 1, mass spectrum data over a predetermined mass-to-charge ratio range can be acquired by scanning a position irradiated with laser light for ionization within a two-dimensional measurement region 50 on a sample 5 such as a biological tissue section, and performing mass spectrometry for each of a large number of measurement points (substantially micro regions) in the measurement region 50. Of course, $MS^n$ analysis (where, n is an integer of greater than or equal to 2) may be enabled by selecting an ion having a specific mass-to-charge ratio and performing a dissociation operation on the selected ion with respect to the ion trapped in the ion trap.

The data analyzing unit 2 receives mass spectrum data (or product ion spectrum data) for each of a large number of measurement points (micro regions) obtained by the imaging mass spectrometry unit 1, and performs analysis processing based on the data. The data analyzing unit 2 includes a spectrum data storage section 20, an image creating section 21, a formula registration processing section 22, a formula storage section 23, an operation condition setting processing section 24, a signal value operation section 25, a post-operation image creating section 26, and a display processing section 27, as functional blocks, to perform characteristic analysis processing described later.

Although the data analyzing unit 2 can be configured by a hardware circuit, the data analyzing unit 2 is generally a computer such as a personal computer or a high-performance workstation. Each of the functional blocks can be embodied by executing, on the computer, dedicated data analysis software installed in the computer. In this case, the input unit 3 is a keyboard or a pointing device (such as a mouse) attached to the computer, and the display unit 4 is a display monitor.

Analyzing Operation in Device of Present Embodiment

In the imaging mass spectrometer of the present embodiment, for example, mass spectrometry imaging data is collected as follows.

The user specifies the measurement region 50 on the sample 5 by the input unit 3, specifies an analysis condition such as a mass-to-charge ratio range of the scan measurement, and then gives an instruction to start the analysis. In response to this, the imaging mass spectrometry unit 1 executes scan measurement over a predetermined mass-to-charge ratio range for each of a large number of measurement points set in the measurement region 50 on the sample 5 to acquire mass spectrum data. The obtained data is transferred from the imaging mass spectrometry unit 1 to the data analyzing unit 2 and stored in the spectrum data storage section 20. When a target component to be observed is determined and the $MS^n$ analysis targeting the target component is desired to be executed in the imaging mass spectrometry unit 1, the molecular weight of the target component or the mass-to-charge ratio of the precursor ion corresponding to the target component and the mass-to-charge ratio range of product ion scan measurement are specified as analysis conditions, and the $MS^n$ analysis according to such conditions may be executed.

Characteristic Analysis Processing in Device of Present Embodiment

When the user desires to confirm the distribution of a specific component on the sample 5, the user specifies a mass-to-charge ratio corresponding to the component with the input unit 3 and then instructs image creation. Then, the image creating section 21 reads out the signal strength corresponding to the specified mass-to-charge ratio in each micro region in the measurement region 50 from the spectrum data storage section 20, converts the signal strength into a display color according to color scale (or gray scale), and creates a heat map-like two-dimensional distribution image. The display processing section 27 displays the created image on the screen of the display unit 4. This image is an MS image.

When it is desired to create a new image by performing a predetermined operation on one or a plurality of MS images, the user registers a formula for the operation or a plurality of auxiliary formulas for creating the formula in advance. An auxiliary formula is a function or the like serving as an element when creating a formula, and the formula can be created by combining a plurality of auxiliary formulas.

For example, when it is desired to perform operation of simply adding two MS images α and β, a formula α+β may be registered. In addition, when it is desired to perform the operation of (α+β)/αβ, a formula of (α+β)/αβ may be registered, two auxiliary formulas of E1=α+β and E2=αβ may be registered, and the formula of (α+β)/αβ may be obtained by specifying the operation of E1/E2 as a combination of these auxiliary formulas.

That is, when the user performs a predetermined operation on the input unit 3, the formula registration processing section 22 displays an input screen of the formula on the display unit 4. On the other hand, when the user inputs the formula or the auxiliary formula, the formula registration processing section 22 stores the formula or the auxiliary formula in the formula storage section 23. Of course, an appropriate formula or auxiliary formula may be stored in the formula storage section 23 at a stage before the device manufacturer provides the present device to the user, in addition to the user himself/herself inputting the formula or auxiliary formula.

Figure 2A:
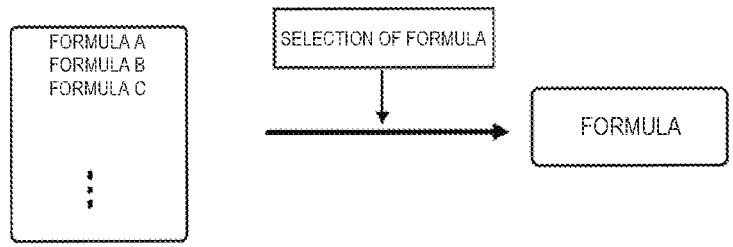
FIGS. 2A and 2B are explanatory diagrams of an example of operation in the imaging mass spectrometer of the present embodiment.
Figure 2B:
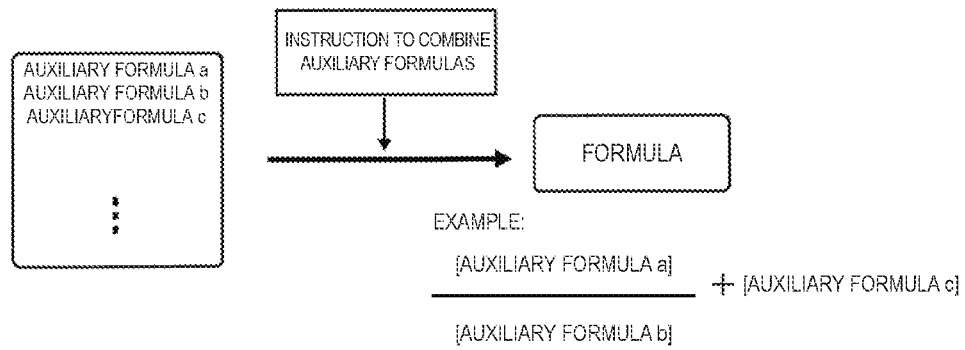
Figure 3:
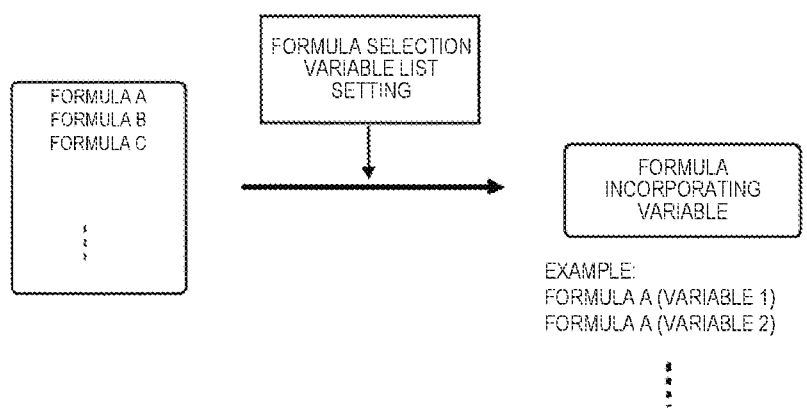
FIG. 3 is an explanatory diagram of an example of operation in the imaging mass spectrometer of the present embodiment.

FIGS. 2A-2B and 3 are explanatory diagrams of an example of operation in the imaging mass spectrometer of the present embodiment.

When creating a new image by a predetermined operation on one or a plurality of MS images, the user specifies one or a plurality of MS images to be processed (or mass-to-charge ratios corresponding thereto), and then selects a formula to be used for the operation from among the formulas registered in the formula storage section 23 (see FIG. 2A). Alternatively, the user selects a plurality of auxiliary formulas registered in the formula storage section 23 and designates a combination thereof (see FIG. 2B). The operation condition setting processing section 24 reads out the formula and the auxiliary formula from the formula storage section 23 according to a selection operation or an instruction operation by the user, and determines the formula to use.

The signal value operation section 25 substitutes, for each micro region constituting one or a plurality of specified MS images, a signal value (ionic intensity value) in a micro region into a determined formula to execute operation processing, and acquires a signal value that is an operation result. The signal value according to the formula is acquired in all the micro regions included in the entire measurement region 50 or the specified range therein. The post-operation image creating section 26 converts the post-operation signal value to a display color according to a color scale (or gray scale) to create a two-dimensional distribution image. The display processing section 27 displays the created image on the screen of the display unit 4. This image is a post-operation distribution image based on one or a plurality of MS images.

Note that the signal value operation section 25 may execute operation not on the ionic intensity value itself as the signal value to be operated but on a value after conversion from the signal strength to the density value (content) according to a calibration curve created in advance.

A specific example of the formula will be described.

Energy Production Accompanying Decomposition of Adenosine Triphosphate

As components that generally exist in a living body, adenosine triphosphate (hereinafter abbreviated as ATP), adenosine diphosphate (hereinafter abbreviated as ADP), and adenosine monophosphate (hereinafter abbreviated as AMP) are known. ATP is a compound that exists as an energy source of all organisms, and ADP and AMP are usually generated by decomposition of ATP. It is known that the amount of energy produced when ATP is decomposed in vivo, that is, the energy production amount E is obtained by the following equation (1) from the abundance of each of ATP, ADP, and AMP.

$$E = P \cdot \{[ATP] + (1/2)[ADP]\} / \{[ATP] + [ADP] + AMP\} \quad (1)$$

where P is a constant. [ATP], [ADP], and [AMP] are the abundance of ATP, ADP, and AMP.

When the relationship between the abundance of ATP, ADP, and AMP and the ionic intensity value obtained by mass spectrometry is linear (that is, the calibration curve is linear), the relative energy production amount can be obtained using equation (1) based on the ionic intensity values corresponding to ATP, ADP, and AMP, respectively. Therefore, for example, as a formula for obtaining the energy production amount based on ATP, ADP, and AMP, a formula of $\{[ATP]+(\frac{1}{2})[ADP]\}/\{[ATP]+[ADP]+AMP\}$ is saved in the formula storage section 23. Then, an image showing the distribution of the relative energy production amount in the biological tissue can be created by obtaining MS images corresponding to ATP, ADP, and AMP, respectively, by imaging mass spectrometry on a sample such as a tissue section, and applying a signal value in each micro region constituting these images to the formula.

Tricarboxylic Acid Cycle (TCA) Circuit

The TCA cycle is one of the most known biochemical reaction circuits related to aerobic metabolism, and is a metabolic pathway that oxidizes the carbon skeleton of sugars, fatty acids, and ketogenic amino acids. Although detailed description is omitted here, it is known that the following reaction is performed in the TCA circuit.

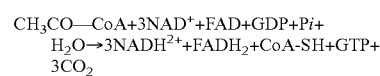

As described above, in the TCA cycle, in the process of oxidizing the carbon skeleton of acetyl CoA, the coenzymes $NAD^+$ and FAD are reduced to produce three molecules of NADH and one molecule of $FADH_2$. In addition, one molecule of GTP that is energetically equivalent to ATP is produced. Therefore, for example, the above-described chemical reaction formula is stored in the formula storage section 23 as a formula, and the signal value in each micro region constituting the MS image corresponding to acetyl CoA or CoA—SH is applied to the formula, whereby an image showing the distribution of GTP and the like can be created.

Pentose Phosphate Pathway

The pentose phosphate pathway is a metabolic pathway starting from glycolytic glucose-6 phosphate, and is involved in the production of various pentoses including NADPH, and sugars essential for biosynthesis of nucleic acids such as deoxyribose and ribose. It is known that the following reaction is performed in the pentose phosphate pathway.

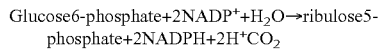

For example, the chemical reaction formula as described above is saved in the formula storage section 23 as a formula, and the signal value in each micro region constituting the MS image corresponding to Glucose 6-phosphate or ribulose 5-phosphate is applied to the formula, whereby an image showing the distribution of NADPH or the like can be created.

In addition, there is a case where it is desired to obtain a new distribution image for each of a plurality of compounds using the same formula. Therefore, in order to respond to this, the variable set in the formula may be input and set by the user in the form of a list. For example, consider a case where it is desired to create a distribution image by calculating C1/(U+V), C2/(U+V), C3/(U+V), . . . (where, U and V are, for example, the abundance of a certain compound) for a plurality of compounds C1, C2, C3, . . . . In this case, when X/(U+V) having a plurality of compounds as a variable X is registered as a formula, and the formula is selected and the variable X is input as a list of mass-to-charge ratios, an operation in which the formula is applied may be performed for each of the MS images at a plurality of mass-to-charge ratios listed in the list (see FIG. 3).

In addition to the calculation formula and the reaction formula, the formula may be a formula for performing logical operations such as logical sum, logical product, and exclusive logical sum of signal strength values or density values for each micro region of a plurality of MS images.

Further Modified Example

In the description of the above embodiment, the image creating section 21 creates the MS image based on the signal strength corresponding to the specified mass-to-charge ratio, but the image creating section may also automatically add signal strengths of other mass-to-charge ratios that are isotopes of compounds corresponding to the specified mass-to-charge ratio, and create the MS image based on the signal strength after the addition. This makes it possible to create an MS image showing a more accurate two-dimensional distribution for the target compound. In order to perform such processing, isotopic information may be given in advance for various compounds.

In addition to creating a new distribution image by applying a formula to an MS image at a specific mass-to-charge ratio or a density image obtained by quantifying the MS image, a new distribution image can be created by applying a formula to various distribution images obtained by mass spectrometry.

Specifically, a new distribution image may be created by applying a formula to an image constituted by signal values obtained by calculation on ionic intensities at different mass-to-charge ratios to each other derived from the same component or a plurality of different components, for example, an image constituted by signal values that are an average of ionic intensities at a plurality of different mass-to-charge ratios derived from the same component.

Furthermore, in the device of the embodiment described above, the measurement region on the sample is two-dimensional, but it is a matter of course that the present invention can also be used in a case where the measurement region is three-dimensional.

Furthermore, although the above embodiment is an example in which the present invention is applied to an imaging mass spectrometer, it is obvious that the present invention can be applied not only to the imaging mass spectrometer but also to various analysis devices capable of analyzing each of a large number of micro regions in a two-dimensional or three-dimensional measurement region on a sample, such as Raman spectroscopic analysis, infrared spectroscopic analysis, and fluorescence analysis, and creating an image based on the results. That is, operation based on a formula may be executed on a Raman spectroscopic image, an infrared spectroscopic image, a fluorescence image, or the like to create a new image.

In addition, instead of executing the operation based on a formula on a plurality of images obtained by the same type of analysis, for example, operation based on a formula may be executed on a plurality of images obtained by different analyses such as an MS image and a Raman spectroscopic image. Of course, in the case of performing such operation processing, it is preferable to perform pre-processing of images such as equalizing the spatial resolution of both images, signal strength correction, and standardization.

Furthermore, the above-described embodiments and modified examples are merely examples of the present invention, and it is a matter of course that modifications, corrections, additions, and the like appropriately made within the scope of the gist of the present invention are included in the claims of the present application.

Various Aspects

The embodiment of the present invention has been described above with reference to the drawings, and lastly, various aspects of the present invention will be described.

An imaging analysis device according to a first aspect of the present invention includes,
an analysis executing section configured to collect data by executing predetermined analysis on each of a plurality of micro regions set in a two-dimensional measurement region on a sample or a three-dimensional measurement region in the sample; a first image creating section configured to use the data obtained by the analysis executing section to create one or a plurality of first distribution images each reflecting a distribution of one or a plurality of specific components included in the sample;
a formula storage section configured to store, as a formula, a chemical reaction formula including at least the one or a plurality of specific components as elements, or either a calculation formula or a logical formula including an amount of the specific component as element;
a signal value calculating section configured to calculate different signal values from the signal values in the micro regions constituting the one or the plurality of first distribution images by using the formula acquired from the formula storage section in response to an instruction of a user; and a second image creating section configured to create a second distribution image based on a calculation result by the signal value calculating section.

According to the first aspect of the present invention, for example, not only is an MS image at a specific mass-to-charge ratio simply displayed, but also a new distribution image, which has not been easily obtained in the related art, configured by signal values calculated by applying various formulas based on a chemical reaction formula or the like can be provided to a user. Specifically, a distribution image reflecting a distribution of another component after the reaction which is assumed to be generated from one or a plurality of specific components by a chemical reaction or a distribution of another component before the reaction which is assumed to generate a specific component by a chemical reaction can be provided to the user. In addition, an image showing the distribution of the energy production amount by a biochemical reaction or the like can be provided to the user. In addition, according to the first aspect of the present invention, various formulas are registered in advance in the formula storage section, and the operation for creating the second image can be performed using the formula selected from the various formulas, so that the work for the analysis processing by the user is simplified.

The imaging analysis device according to a second aspect of the present invention is such that, in the first aspect, a plurality of auxiliary formulas, each of which is an element constituting a formula, are stored in the formula storage section, and the signal value calculating section can combine a plurality of auxiliary formulas acquired from the formula storage section according to an instruction of a user to constitute a target formula, and calculate another signal value using the formula.

According to the second aspect of the present invention, registration work of a complicated formula can be simplified.

The imaging analysis device according to a third aspect of the present invention is such that, in the first aspect, a formula including a variable is stored in the formula storage section, and the signal value calculating section can create a plurality of formulas in which different first distribution images are associated with the variable of the formula acquired from the formula storage section according to an instruction of a user, and calculate different signal values using the plurality of formulas.

According to the third aspect of the present invention, the second distribution images with respect to a plurality of different first distribution images can be efficiently acquired with a simple operation.

The imaging analysis device according to a fourth aspect of the present invention is such that, in any one of the first to third aspects, the predetermined analysis may be mass spectrometry.

REFERENCE SIGNS LIST

1 . . . Imaging Mass Spectrometry Unit
2 . . . Data Analyzing Unit
20 . . . Spectrum Data Storage Section
21 . . . Image Creating Section
22 . . . Formula Registration Processing Unit
23 . . . Formula Storage Section
24 . . . Operation Condition Setting Processing Unit
25 . . . Signal Value Operation Section
26 . . . Post-Operation Image Creating Section
27 . . . Display Processing Section
3 . . . Input Unit
4 . . . Display Unit

The invention claimed is:

1. An imaging analysis device comprising:
an analysis executing section configured to collect data by executing predetermined analysis on each of a plurality of micro regions set in a two-dimensional measurement region on a sample or a three-dimensional measurement region in the sample;
a formula storage section configured to store, as a formula which is either a chemical reaction formula including a plurality of specific components as elements, or either a calculation formula or a logical formula including an amount of the plurality of specific components as an element;
a first image creating section configured to extract data corresponding to the plurality of specific components from the data obtained by the analysis executing section and to create a plurality of first distribution images each of which represents a distribution of one of the plurality of specific components included in the sample;
a signal value calculating section configured to calculate a signal value at each of the plurality of micro regions from the signal values at a corresponding micro region in the plurality of first distribution images by using the formula stored in the formula storage section; and
a second image creating section configured to create a second distribution image based on a calculation result by the signal value calculating section.

2. The imaging analysis device according to claim 1, wherein a plurality of auxiliary formulas, each of which is an element constituting a formula, are stored in the formula storage section; and the signal value calculating section combines a plurality of auxiliary formulas acquired from the formula storage section according to an instruction of a user to constitute a target formula, and calculates another signal value using the target formula.

3. The imaging analysis device according to claim 1, wherein a formula including a variable is stored in the formula storage section; and the signal value calculating section creates a plurality of formulas in which different first distribution images are associated with the variable of the formula acquired from the formula storage section according to an instruction of a user, and calculates different signal values using the plurality of formulas.

4. The imaging analysis device according to claim 1, wherein the predetermined analysis is mass spectrometry.

5. The imaging analysis device according to claim 1, wherein the second distribution image (i) reflects a distribution of a plurality of derived components, the plurality of derived components being different than the plurality of specific components, (ii) is a metabolic energy production distribution image or (iii) is a metabolic energy consumption distribution image.

6. The imaging analysis device according to claim 1, wherein the one of the plurality of specific components included in the sample include one of adenosine triphosphate (ATP), adenosine diphosphate (ADP), or adenosine monophosphate (AMP), and
wherein the second distribution image reflects a distribution of relative energy production in the two-dimensional measurement region on the sample or the three-dimensional measurement region in the sample.

7. The imaging analysis device according to claim 1,
wherein the one of the plurality of specific components included in the sample include one of oxidized acetyl coenzyme A (CoA) or reduced acetyl coenzyme A (CoA-SH), and
wherein the second distribution image reflects a distribution of at least one of guanosine triphosphate (GTP) or guanosine diphosphate (GDP).

8. The imaging analysis device according to claim 1,
wherein the one of the plurality of specific components included in the sample include one of glucose 6-phosphate or ribulose 5-phosphate, and
wherein the second distribution image reflects a distribution of at least one of reduced nicotinamide adenine dinucleotide phosphate (NADPH) or oxidized nicotinamide adenine dinucleotide phosphate (NADP$^+$).

* * * * *